US010343156B2

(12) United States Patent
Staton et al.

(10) Patent No.: US 10,343,156 B2
(45) Date of Patent: Jul. 9, 2019

(54) TAPERED PIPETTE

(71) Applicant: Nalge Nunc International Corporation, Rochester, NY (US)

(72) Inventors: John M. Staton, Fairport, NY (US); Daniel J. Dwyer, Macedon, NY (US)

(73) Assignee: Nalge Nunc International Corporation, Rochester, NY (US)

( * ) Notice: Subject to any disclaimer, the term of this patent is extended or adjusted under 35 U.S.C. 154(b) by 300 days.

(21) Appl. No.: 13/835,663

(22) Filed: Mar. 15, 2013

(65) Prior Publication Data

US 2014/0260697 A1 Sep. 18, 2014

(51) Int. Cl.
B01L 3/02 (2006.01)
G01N 1/10 (2006.01)

(52) U.S. Cl.
CPC ............ B01L 3/021 (2013.01); B01L 3/0275 (2013.01); G01N 1/10 (2013.01); B01L 2200/0605 (2013.01)

(58) Field of Classification Search
CPC ..................................................... G01N 1/10
USPC ............... 73/864.01–864.11, 864.15–864.16, 73/864.22–864.25
See application file for complete search history.

(56) References Cited

U.S. PATENT DOCUMENTS

| 3,084,592 | A | 4/1963 | Scott |
| D198,263 | S | 5/1964 | Tietje |
| D204,352 | S | 4/1966 | Eizenberg |
| D228,492 | S | 10/1973 | Cohen |
| D229,748 | S | 1/1974 | White |
| 3,815,790 | A | 6/1974 | Allen et al. |
| 3,938,392 | A | 2/1976 | Rodrigues |
| D246,380 | S | 11/1977 | Boothby |

(Continued)

FOREIGN PATENT DOCUMENTS

| WO | 2007071088 A1 | 6/2007 |
| WO | 2010028712 A1 | 3/2010 |

OTHER PUBLICATIONS

European Patent Office, International Search Report and Written Opinion of the International Searching Authority, International Application No. PCT/US2014/024398, dated Jun. 3, 2014 (9 pages).

(Continued)

*Primary Examiner* — Peter J Macchiarolo
*Assistant Examiner* — Anthony W Megna Fuentes
(74) *Attorney, Agent, or Firm* — Wood Herron & Evans LLP

(57) ABSTRACT

Described are pipettes capable of dispensing both high volumes of liquid and highly accurate smaller volumes of liquid wherein the accuracy of the volume of liquid delivered increases along the length of the pipette. Embodiments of the pipette include an elongated body with an outer surface, an inner surface defining a lumen within the elongated body, a proximal orifice at a proximal end, a distal orifice at a distal end. The intermediate portion includes a first generally frustoconical-shaped portion defined by a first inner diameter proximate the proximal end of the elongated body and a second inner diameter proximate a second end thereof. In an embodiment, the intermediate portion includes a second generally frustoconical-shaped portion defined by a third inner diameter proximate the transition to the first portion and a fourth inner diameter adjacent the distal end of the elongated body.

29 Claims, 13 Drawing Sheets

(56) References Cited

U.S. PATENT DOCUMENTS

| | | |
|---|---|---|
| D250,599 S | 12/1978 | St. Amand |
| D252,586 S | 8/1979 | Kovach |
| D254,445 S | 3/1980 | Boghosian |
| D255,601 S | 6/1980 | De Vaughn |
| D256,052 S | 7/1980 | De Vaughn |
| D257,567 S | 11/1980 | Peacock |
| D257,791 S | 1/1981 | Parker |
| D260,434 S | 8/1981 | St. Amand |
| D260,554 S | 9/1981 | Roach |
| D266,874 S | 11/1982 | St. Amand |
| D268,131 S | 3/1983 | St. Amand |
| RE31,555 E | 4/1984 | Garren et al. |
| D274,651 S | 7/1984 | De Vaughn |
| D274,652 S | 7/1984 | DeVaughn |
| 4,483,825 A | 11/1984 | Fatches |
| D286,570 S | 11/1986 | Williams |
| 4,647,419 A | 3/1987 | Helfer et al. |
| D292,827 S | 11/1987 | Fele |
| D297,054 S | 8/1988 | Williams |
| 4,779,768 A | 10/1988 | St. Amand |
| D299,956 S | 2/1989 | Saint-Amand |
| D300,561 S | 4/1989 | Asa et al. |
| D303,151 S | 8/1989 | Saint-Amand |
| D303,152 S | 8/1989 | Saint-Amand |
| 4,877,585 A | 10/1989 | Perlman |
| 5,032,343 A | 7/1991 | Jeffs et al. |
| 5,084,241 A | 1/1992 | Parker |
| D326,322 S | 5/1992 | Clegg et al. |
| 5,156,811 A | 10/1992 | White |
| D333,705 S | 3/1993 | Garren et al. |
| 5,223,225 A | 6/1993 | Gautsch |
| 5,232,669 A | 8/1993 | Pardinas |
| 5,240,397 A | 8/1993 | Fay et al. |
| D357,324 S | 4/1995 | Bartal |
| D358,464 S | 5/1995 | Anderson |
| D362,387 S | 9/1995 | Shumer |
| D365,146 S | 12/1995 | Olson |
| 5,496,523 A | 3/1996 | Gazit et al. |
| 5,516,564 A | 5/1996 | Root et al. |
| D373,827 S | 9/1996 | Polaniec |
| 5,563,356 A | 10/1996 | Mussi et al. |
| D384,162 S | 9/1997 | Husar et al. |
| D384,163 S | 9/1997 | Husar et al. |
| D384,418 S | 9/1997 | Torti et al. |
| D386,260 S | 11/1997 | Polaniec |
| D387,425 S | 12/1997 | Niedospial et al. |
| D387,426 S | 12/1997 | Husar et al. |
| 5,770,158 A | 6/1998 | Eischen et al. |
| 5,779,984 A * | 7/1998 | Kelly .................. B65D 25/108 206/486 |
| D401,698 S | 11/1998 | Daniels |
| D405,882 S | 2/1999 | Yale |
| D414,562 S | 9/1999 | Tajima |
| D416,625 S | 11/1999 | Torti et al. |
| D425,617 S | 5/2000 | Snedden |
| 6,066,297 A | 5/2000 | Torti et al. |
| 6,168,761 B1 | 1/2001 | Kelly et al. |
| D437,797 S | 2/2001 | Bishop |
| D437,940 S | 2/2001 | Rainin et al. |
| D438,629 S | 3/2001 | Stevens |
| D438,954 S | 3/2001 | Orsing |
| D438,981 S | 3/2001 | Rainin et al. |
| D439,986 S | 4/2001 | Petrek |
| D441,458 S | 5/2001 | Petrek |
| 6,224,588 B1 | 5/2001 | Jentzen |
| D443,364 S | 6/2001 | Stevens |
| D445,495 S | 7/2001 | Schaefer et al. |
| D446,864 S | 8/2001 | Petrek |
| D448,853 S | 10/2001 | Rainin et al. |
| D461,904 S | 8/2002 | Petrek |
| D465,844 S | 11/2002 | Anderson et al. |
| D465,853 S | 11/2002 | Petersen |
| 6,482,362 B1 | 11/2002 | Smith |
| D468,024 S | 12/2002 | Petrek |
| D468,439 S | 1/2003 | On et al. |
| D468,440 S | 1/2003 | Petrek |
| D468,830 S | 1/2003 | On et al. |
| D468,831 S | 1/2003 | On et al. |
| D468,832 S | 1/2003 | Petrek |
| 6,550,349 B1 | 4/2003 | Godin |
| 6,566,145 B2 | 5/2003 | Brewer |
| 6,589,484 B2 | 7/2003 | Buehler |
| 6,596,240 B2 | 7/2003 | Taggart et al. |
| D487,593 S | 3/2004 | Sarna |
| 6,737,023 B1 | 5/2004 | Kelly et al. |
| 6,837,119 B2 | 1/2005 | Blackwood-Sewell |
| 6,955,077 B2 | 10/2005 | Blaszcak et al. |
| 7,047,828 B2 | 5/2006 | Blaszcak et al. |
| 7,081,228 B1 | 7/2006 | Ito |
| 7,185,551 B2 | 3/2007 | Schwartz |
| D560,815 S | 1/2008 | Tajima |
| 7,320,259 B2 | 1/2008 | Jessop |
| D561,347 S | 2/2008 | Tajima |
| D561,906 S | 2/2008 | Tajima |
| D565,192 S | 3/2008 | Tajima |
| D569,989 S | 5/2008 | Tajima |
| D593,205 S | 5/2009 | Ayliffe |
| D601,712 S | 10/2009 | Tajima |
| 8,133,454 B2 | 3/2012 | Tajima |
| 8,163,256 B2 | 4/2012 | Cote et al. |
| D663,042 S | 7/2012 | Motadel et al. |
| 8,211,386 B2 | 7/2012 | Talmer et al. |
| D673,291 S | 12/2012 | Knight et al. |
| D679,826 S | 4/2013 | Ziegmann et al. |
| D679,828 S | 4/2013 | Motadel et al. |
| D680,226 S | 4/2013 | Motadel et al. |
| 8,425,860 B2 | 4/2013 | Tajima |
| 8,476,080 B2 | 7/2013 | Talmer et al. |
| D687,562 S | 8/2013 | Motadel et al. |
| D687,563 S | 8/2013 | Tamura |
| D690,417 S | 9/2013 | Solomon |
| D691,282 S | 10/2013 | Motadel et al. |
| D694,424 S | 11/2013 | Kwak et al. |
| D699,837 S | 2/2014 | Ericsson |
| D700,318 S | 2/2014 | Amoah et al. |
| D703,344 S | 4/2014 | Herbst et al. |
| D706,946 S | 6/2014 | Lohn |
| D709,623 S | 7/2014 | Lohn |
| 8,828,331 B2 | 9/2014 | Tajima |
| 2006/0171851 A1 | 8/2006 | Motadel |
| 2006/0177352 A1 | 8/2006 | Ziegmann et al. |
| 2007/0017870 A1 | 1/2007 | Belov et al. |
| 2007/0231215 A1 | 10/2007 | Mototsu et al. |
| 2008/0078258 A1 | 4/2008 | Price et al. |
| 2008/0286157 A1* | 11/2008 | Mathus .................. B01L 3/0279 422/513 |
| 2008/0292505 A1 | 11/2008 | Tian |
| 2009/0158861 A1* | 6/2009 | Tanner ....................... 73/864.11 |
| 2010/0218622 A1 | 9/2010 | Motadel |
| 2011/0129396 A1 | 6/2011 | Fish |
| 2011/0183433 A1 | 7/2011 | Motadel et al. |
| 2011/0263005 A1 | 10/2011 | Chang et al. |
| 2012/0213677 A1* | 8/2012 | Petrek ..................... B01L 3/022 422/525 |

OTHER PUBLICATIONS

Espacenet, International Application No. WO2007/071088A1, Published on Jun. 28, 2007, retrieved from http://worldwide.espacenet.com on Jun. 12, 2014 (9 pages).

www.colepalmer.com, Corning Stripette Serological Pipettes, 10.0 mL, Individually Wrapper Paper/Plastic Banana Peel, 2011, 2 pages.

www.colepalmer.com, Pyrex 7078 Pipette, 10ML, 720/CS, 2011, 2 pages.

www.colepalmer.com, 5 mL Cole-Parmer large-tip opening serological pipette (YO-25562-24), 2011, 3 pages.

Photograph of Turkey Baster against a ruler, date unknown, 1 page.

Intellectual Property Office of Singapore, Written Opinion issued in corresponding Singapore Application No. 11201507498W, dated May 18, 2016 (6 pages).

State Intellectual Property Office of the People's Republic of China, First Office Action and Search Report issued in corresponding

(56) References Cited

OTHER PUBLICATIONS

Chinese Application No. 201480026402.7, English Translation, dated Jul. 13, 2016 (5 pages).

* cited by examiner

TAPERED PIPETTE

FIELD

The present invention is directed to a pipette for dispensing a volume of liquid and, more particularly, to a pipette with a tapered body for accurately dispensing a volume of a liquid.

BACKGROUND

Pipettes are used to dispense known volumes of liquid. Typically, a vacuum is applied to the mouth piece end of the pipette to draw a volume of liquid into the lumen of the pipette from a liquid reservoir, such as a bottle. Portions of the volume of liquid are then dispensed to one or more other containers. In many instances, exact volumes liquid must be accurately dispensed. To this end, many pipettes include graduations that indicate the volume of liquid in the lumen of the pipette, e.g., 1 milliliter (ml), 0.1 ml, etc. The internal diameter of the pipette determines the volume of the lumen at a given length of the pipette. The accuracy of the graduations is likewise determined at least in part by the internal diameter of the lumen of the pipette. Pipettes having a smaller internal diameter may more accurately dispense smaller volumes of liquid than pipettes with a larger internal diameter because the smaller volume is spread over a greater length of the pipette. However, the total volume of liquid capable of being dispensed by a pipette with a small internal diameter generally is limited by the practical length of the pipette. The practical length of a pipette is typically limited by the ability of the user to operate the pipette. For example, many pipettes are operated in a ventilated hood environment having a limited workspace area. Pipettes over a certain length are not practical for use in such an environment. Thus, highly accurate pipettes, such as those used to accurately dispense fractions of a milliliter, have a small internal diameter with a very limited volume.

In contrast to the exacting requirements for accurately dispensing very small volumes, in some uses the dispensed volume is not required to be as accurately dispensed, such as when dispensing multiple volumes of 1 ml or more. In these circumstances, a less accurate pipette with a larger internal diameter may be used.

In response to the various needs of different users, many manufacturers produce pipettes in a variety of maximum volume capacities, such as 1 ml, 2 ml, 5 ml, 10 ml, 25 ml, 50 ml, and 100 ml volumes. Larger volume pipettes sacrifice dispensing accuracy for increased volume. Likewise, highly accurate dispensing pipettes sacrifice volume for accuracy. Most laboratories have a mixed need for highly accurate and high volume pipettes. As such, these laboratories will typically stock a variety of different pipettes to meet its needs. The need to stock multiple sizes of pipettes can present stocking problems for the laboratory.

Perlman, U.S. Pat. No. 4,877,585, attempted to solve this problem by providing a graduated pipette with a generally cylindrical upper tube capable of delivering large volumes joined to a generally cylindrical lower tube with a smaller internal diameter for delivering small volumes. The upper and lower tubes are separately formed and then joined together with a cylindrical connector or by being welded together. Tubes that are joined together in these fashions may fail at the site of the connector or weld causing leakage, or even more detrimentally, causing the lower tube to fall away from the upper tube. In addition, the generally cylindrical upper and lower tubes each deliver a constant volume of liquid per unit of length of the respective tube. Thus, outside of the transition between the two tubes, the accuracy of the graduated markings on the individual tubes remains constant. A need for a unitary pipette with increased dispensing accuracy near the tip of the pipette compared to the dispensing accuracy nearer the mouthpiece was identified.

One method of making pipettes utilizes injection molding. However, injection molding processes inject thermoplastic materials under very high pressures into the mold. The high pressure injection of thermoplastic materials imparts significant forces at the injections site on the core used to form the lumen of the pipette during the injection process. As discussed above, highly accurate pipettes have a lumen with a relatively small internal diameter. Accordingly, the core of the injection mold necessarily has a relatively small external diameter. The high pressure imparted on the core can result in deflection of the core during the injection process. Core deflection can decrease the accuracy of the resulting pipette. Fay et al., U.S. Pat. No. 5,240,397 addressed the core deflection problem with a complicated injection molding process that used paired retractable locking pins for stabilizing the core during injection, solenoid drives for extending and contracting the pins, and a controller for retracting the pins as the injected resin flows along the core to the space proximate the pins. A need for a simple method of producing a highly accurate injection molded pipette to correct the deflection problem was identified.

In addition to concerns relating to the deflection of the thin core needed for highly accurate pipettes, there is also a risk of core breakage during removal of the pipette body. As the injected resin cools, it shrinks onto the core. Long thin core pins use to generate highly accurate pipettes are subject to locking forces as the resin cools. When the cooling pipette is removed from the core, these locking forces can cause the long thin cores to break. A need for a method of producing a highly accurate injection molded pipette with a decreased risk of breaking the core was identified.

SUMMARY

Pipettes are needed that are capable of dispensing both high volumes of liquid and highly accurate smaller volumes of liquid wherein the accuracy of the volume of liquid delivered increases along the length of the pipette. Also needed are pipettes having a one-piece construction that are capable of dispensing both high volumes of liquid and highly accurate smaller volumes of liquid wherein the accuracy of the volume of liquid delivered increases along the length of the pipette. To this end, described are pipettes capable of dispensing both high volumes of liquid and highly accurate smaller volumes of liquid wherein the accuracy of the volume of liquid delivered increases along the length of the pipette. Also described herein are pipettes with a body having a one-piece construction that is capable of dispensing both high volumes of liquid and highly accurate smaller volumes of liquid wherein the accuracy of the volume of liquid delivered increases along the length of the pipette.

Embodiments also address concerns relating to core deflection during the injection molding process by having a relatively thick core near the injection site near the proximal end of the pipette that tapers along the length of the pipette toward the opening in the tip of the pipette. In addition, the taper allows for the cooling pipette to simultaneously release the core when being removed from the core thereby decreasing the risk of core breakage during this step.

In an embodiment, the pipette includes an elongated polymeric body with an outer surface, an inner surface defining a lumen within the elongated body, a proximal orifice at a proximal end of the elongated body, a distal orifice at a distal end of the elongated body, and an intermediate portion extending between the proximal and distal orifices. The intermediate portion includes a first generally frustoconical-shaped portion. The first generally frustoconical-shaped portion is defined by a first inner diameter proximate one end thereof adjacent the proximal end of the elongated body and a second inner diameter proximate a second end thereof defining the transition to the second generally frustoconical portion. The first inner diameter is greater than the second inner diameter. The distal orifice has a diameter in the range between about 1 millimeter and about 3 millimeters.

In another embodiment, the intermediate portion includes a second generally frustoconical shaped portion. The second generally frustoconical-shaped portion may be contiguous with the first generally frustoconical-shaped portion. The second generally frustoconical shaped portion is defined by a third inner diameter proximate one end thereof and a fourth inner diameter proximate a second end thereof adjacent the distal end of the elongated body. The third inner diameter is greater that the fourth inner diameter.

BRIEF DESCRIPTION OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

Figure 1A:
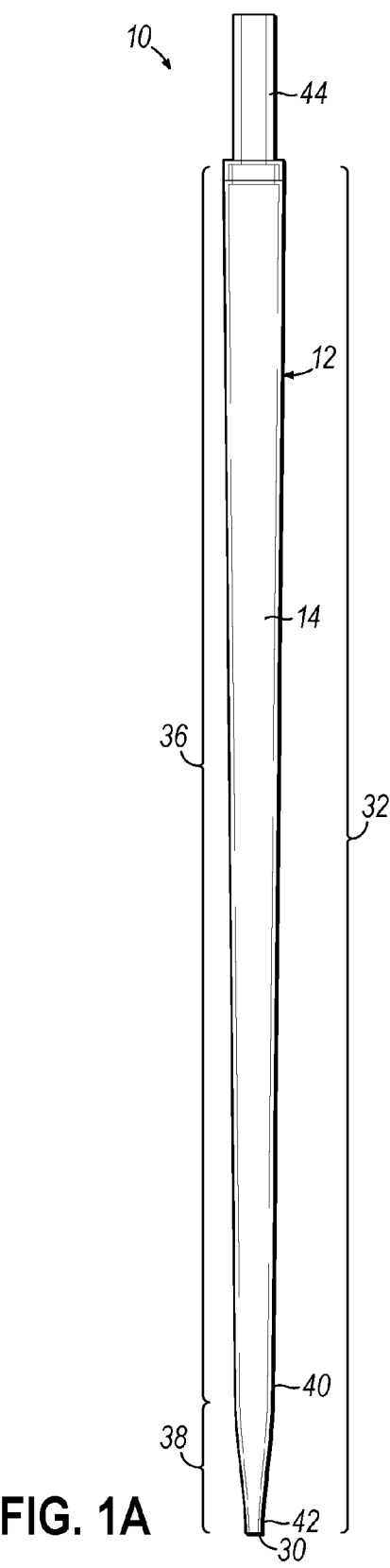
FIG. 1A is an elevated view of a pipette in accordance with embodiments of the invention.
Figure 1B:
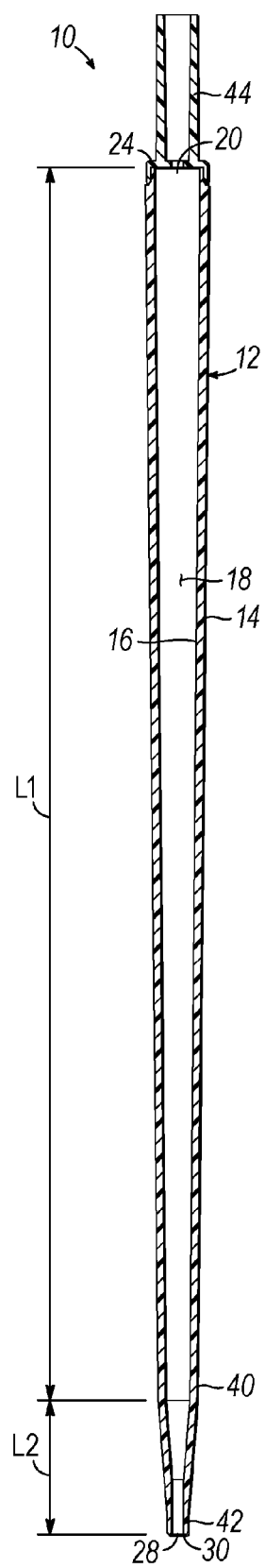
FIG. 1B is a cross section of the pipette of FIG. 1A
Figure 1C:
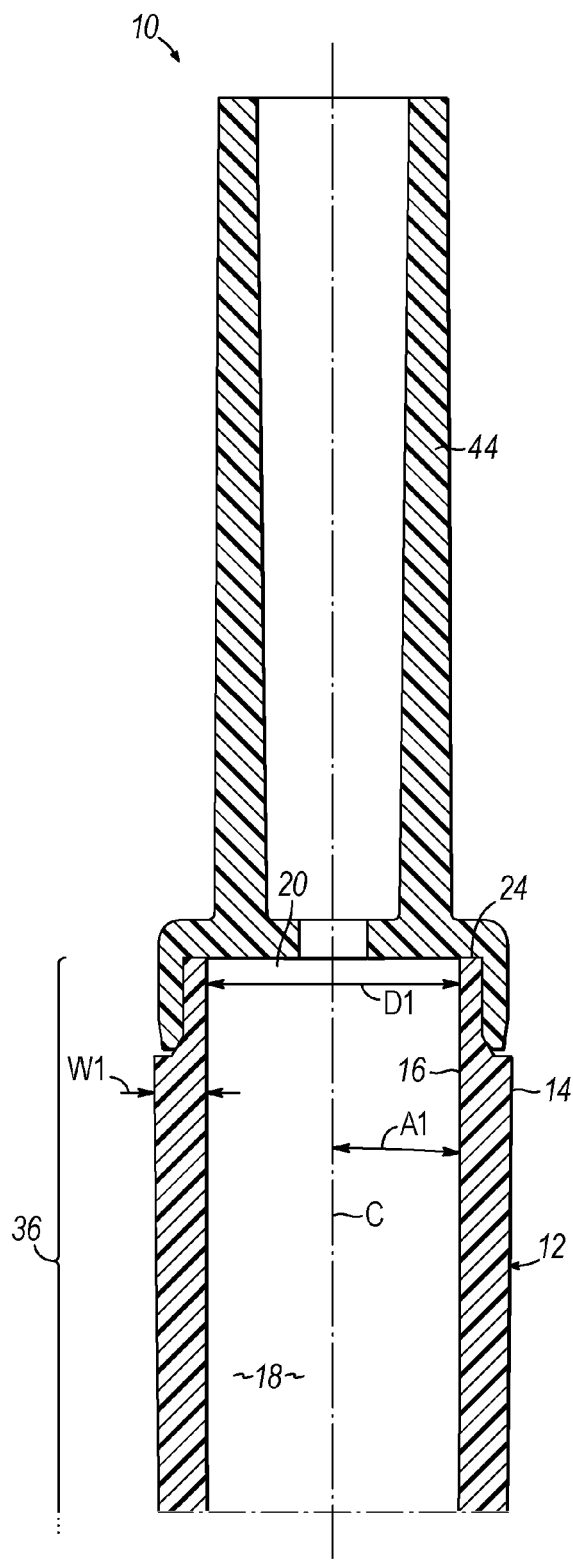
FIG. 1C is a magnified view of an end of the pipette of FIG. 1B.
Figure 1D:
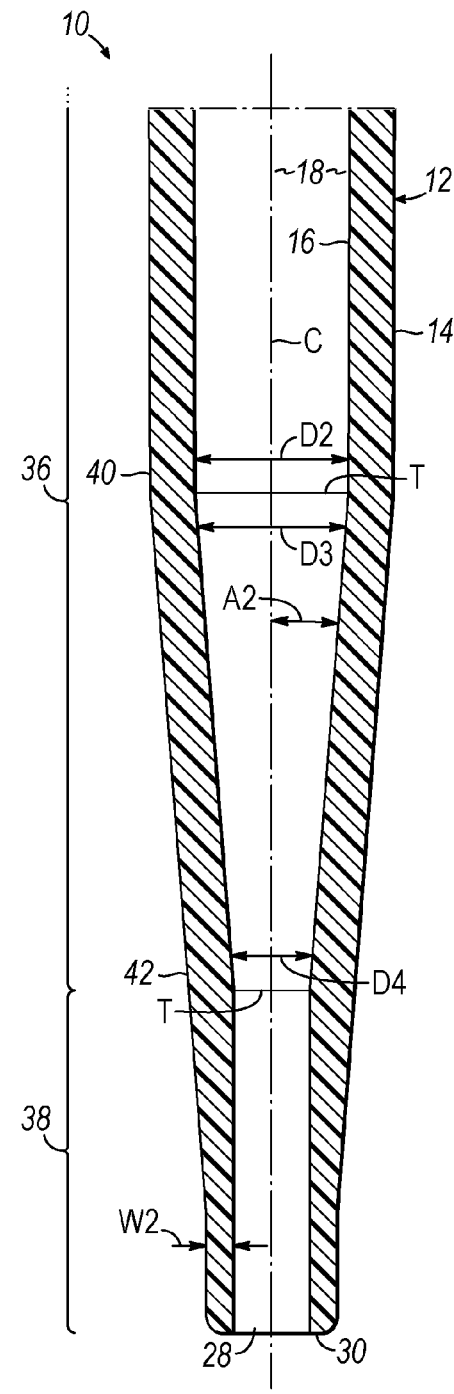
FIG. 1D is a magnified view of an end of the pipette of FIG. 1B.

FIGS. 1A-1D, 2A-2D, 3A-3D, 5A-5D, and 6A-6E illustrate embodiments of pipettes 10, 110, and 210 in accordance with principles of the invention. The pipette 10, 210, 220 has an elongated polymeric body 12, 112, 212, with an outer surface 14, 114, 214, an inner surface 16, 116, 216, defining a lumen 18, 118, 218 within the elongated body, a proximal orifice 20, 120, 220 at a proximal end 24, 124, 224 of the elongated body, a distal orifice 28, 128, 228 at a distal end 30, 130, 230 of the elongated body, and an intermediate portion 32, 132, 232 extending between the proximal orifice 20, 120, 220 and the distal orifice 28, 128, 228.

The intermediate portion 32, 132, 232 has a first generally frustoconical-shaped portion 36, 136, 236 and a second generally frustoconical-shaped portion 38, 138, 238. In an embodiment illustrated in FIGS. 1A-1D, 2A-2D, and 3A-3D, the first generally frustoconical-shaped portion 36, 136, 236 defines a first taper and the second generally frustoconical-shaped portion 38, 138, 238 defines a second taper. In an embodiment, the first generally frustoconical-shaped portion 36, 136, 236 is contiguous with the second generally frustoconical-shaped portion 38, 138, 238.

Figure 2A:
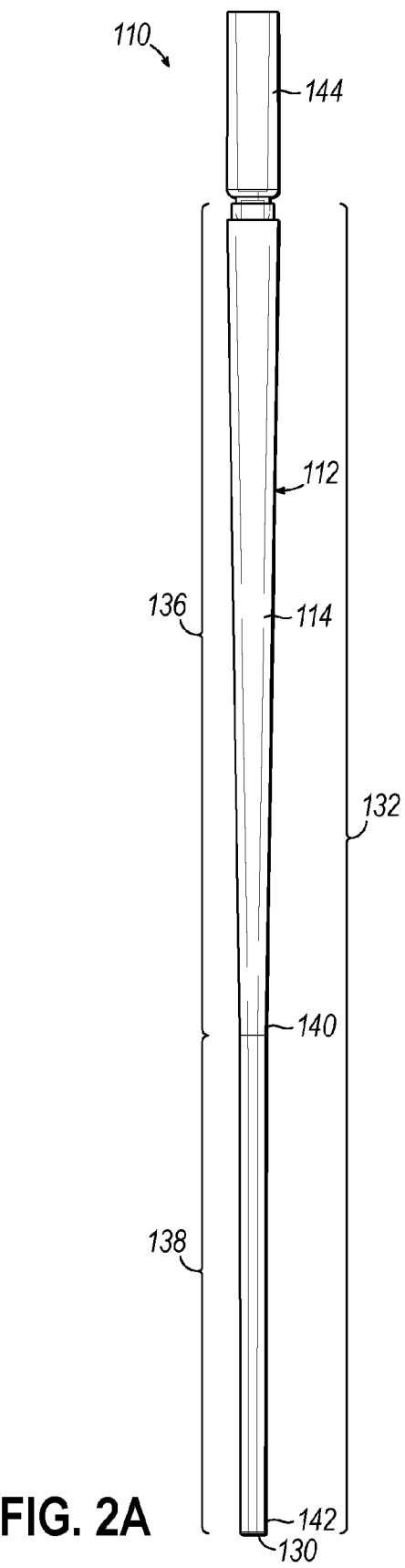
FIG. 2A is an elevated view of a pipette in accordance with embodiments of the invention.
Figure 2B:
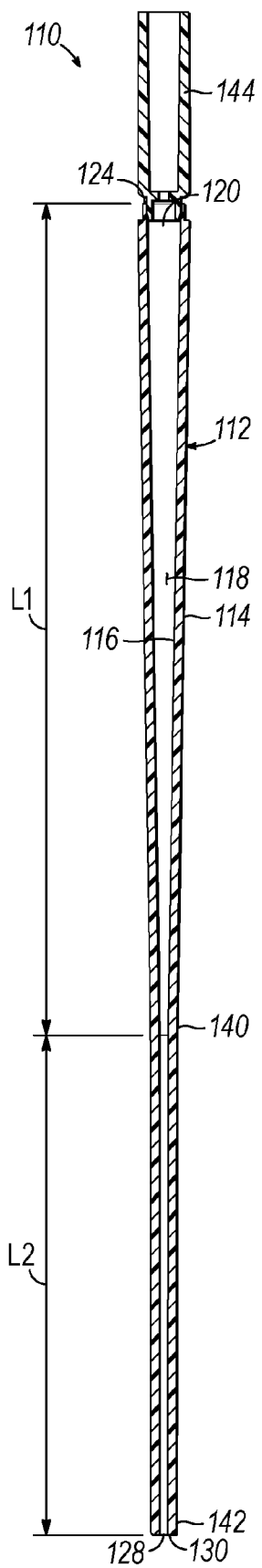
FIG. 2B is a cross section of the pipette of FIG. 2A
Figure 2C:
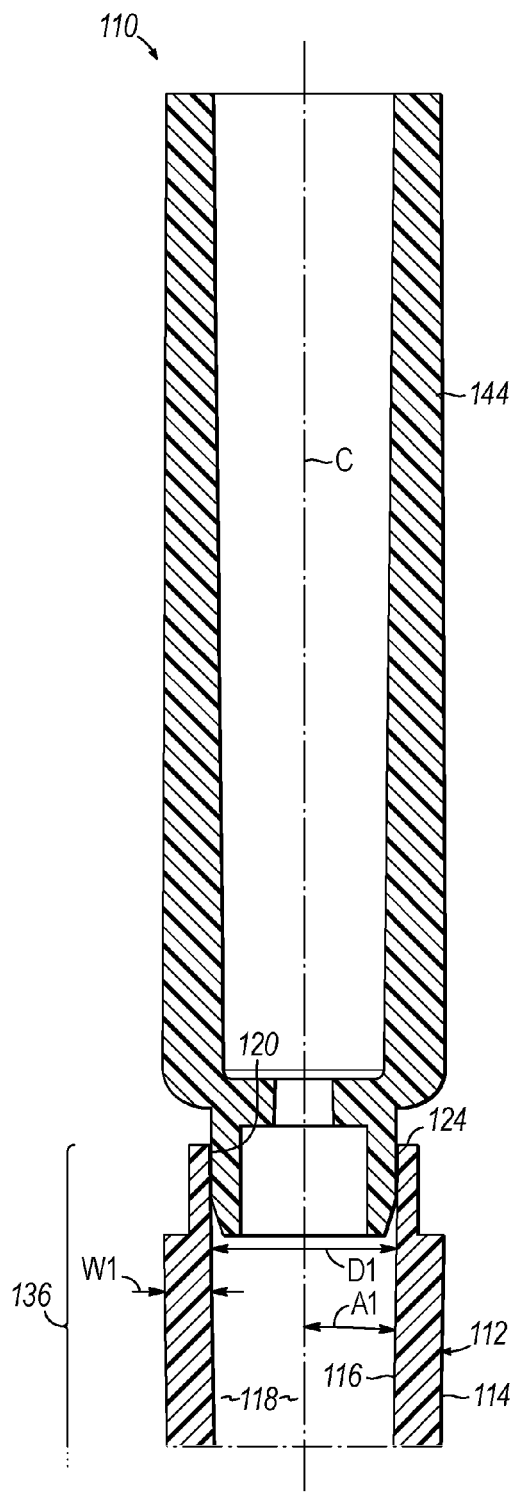
FIG. 2C is a magnified view of an end of the pipette of FIG. 2B.
Figure 2D:
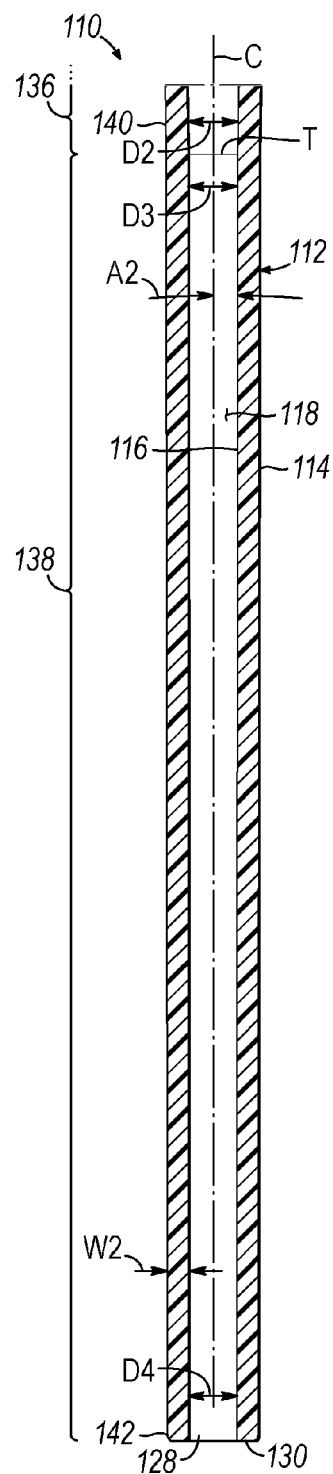
FIG. 2D is a magnified view of an end of the pipette of FIG. 2B.
Figure 3A:
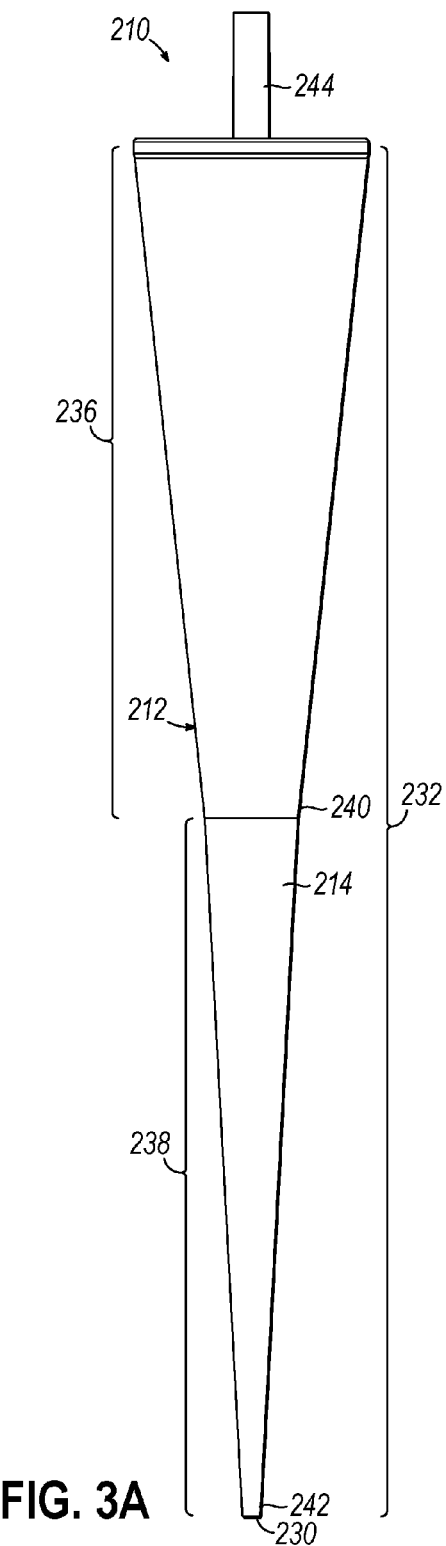
FIG. 3A is an elevated view of a pipette in accordance with embodiments of the invention.
Figure 3B:
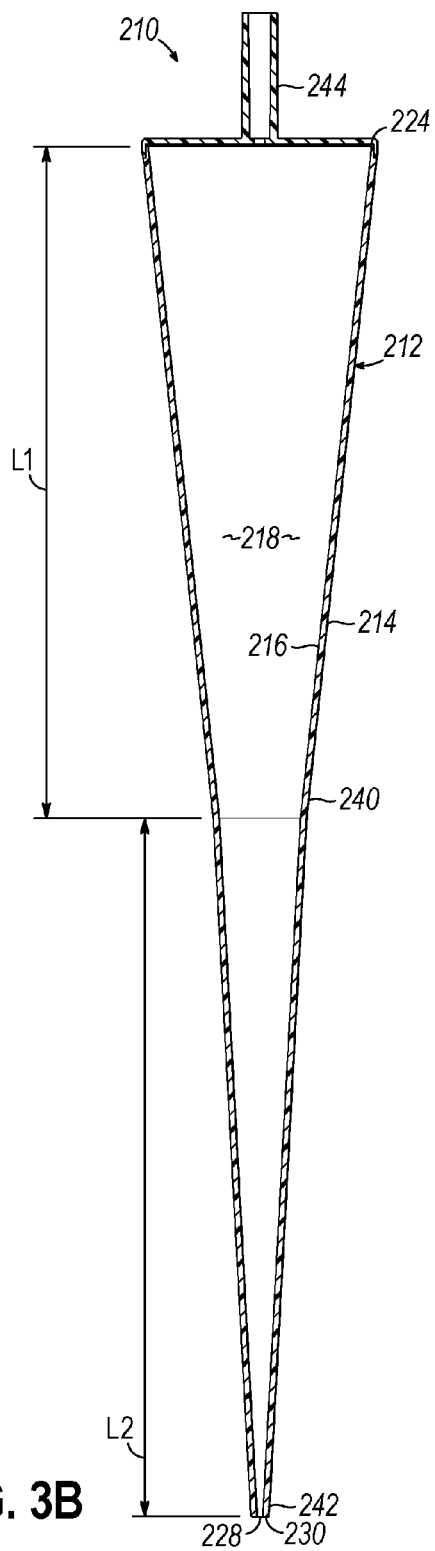
FIG. 3B is a cross section of the pipette of FIG. 3A
Figure 3C:
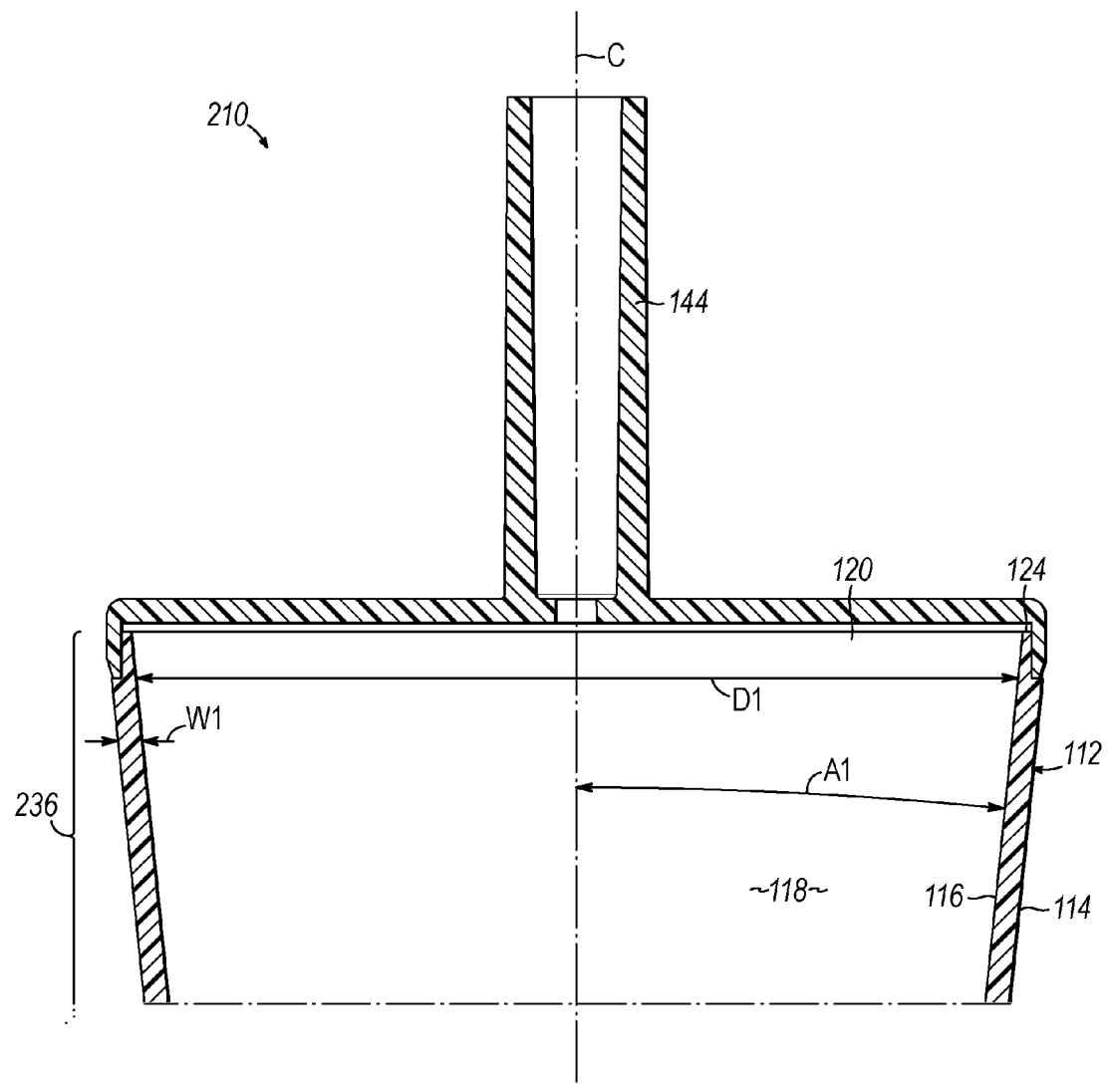
FIG. 3C is a magnified view of an end of the pipette of FIG. 3B.
Figure 3D:
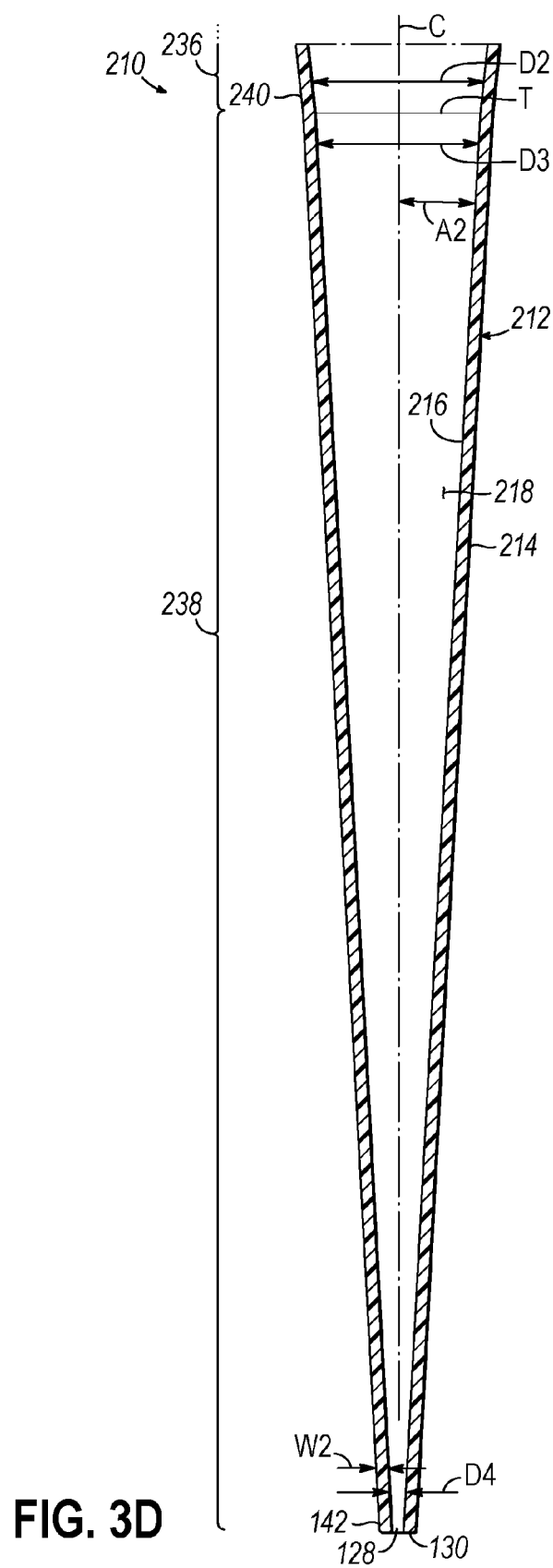
FIG. 3D is a magnified view of an end of the pipette of FIG. 3B.

In another embodiment illustrated in FIGS. 5A-5D, pipette 410 is similar to the pipettes illustrated FIGS. 1A, 2A, and 3A except that the intermediate portion 432 of the elongated body 412 includes only a first generally frustoconical shaped portion 436 that extends between the distal end 424 and the proximal end 430 of the elongated body 412. The pipette has an outer surface 414 and in inner surface 416 defining a lumen 418 within the elongated body 412, a proximal orifice 420 at a proximal end 424 and a distal orifice 428 at a distal end 430 which is proximate the second end 440 of the elongated body 412. The internal diameter of the distal orifice 430 ranges from about 1 mm to about 3 mm.

In yet another embodiment illustrated in FIG. 6A-6E, pipette 510 is similar to the pipettes illustrated FIGS. 1A, 2A, 3A, 4A except that the pipette includes one or more additional sections, such as a third generally frustoconical-shaped portion 546. The pipette has an outer surface 514 and in inner surface 516 defining a lumen 518 within the elongated body 512, a proximal orifice 520 at a proximal end 524 and a distal orifice 528 at a distal end 530 which is proximate the second end 540 of the elongated body 512. The internal diameter of the distal orifice 530 ranges from about 1 mm to about 3 mm.

With reference to FIGS. 1A-1D, 2A-2D, 3A-3D, 5A-5D, and 6A-6E, the first generally frustoconical-shaped portion 36, 136, 236, 436, 536 is defined by a first inner diameter D1 proximate one end thereof adjacent the proximal end 24, 124, 224, 424, 524 of the elongated body 12, 112, 212, 412, 512 and a second inner diameter D2 proximate a second end 40, 140, 240, 440, 540 of the first generally frustoconical-shaped portion 36, 136, 236, 436, 536. In embodiments wherein the first generally frustoconical-shaped portion 36, 136, 236, 536 is contiguous with the second generally frustoconical shaped portion 38, 138, 238, 538, the second inner diameter D2 defines the transition T between the first generally frustoconical-shaped portion 36, 136, 236, 536 and the second generally frustoconical-shaped portion 38, 138, 238, 538. In embodiments wherein the first generally frustoconical-shaped portion 36, 136, 236, 536 and the second generally frustoconical-shaped portion are separated by one or more additional sections, D2 is adjacent the one or more additional sections.

The first inner diameter D1 is greater than the second inner diameter D2. The first inner diameter D1 is in a range from about 4 mm to about 50 mm. In another embodiment, the first inner diameter D1 is in a range from about 4 mm to 25 mm and in a further embodiment, the first inner diameter is in a range from about 30 mm to about 50 mm.

The second inner diameter D2 is in a range from about 3.5 mm to about 20 mm. In another embodiment, the second inner diameter D2 is in a range from about 3.5 mm to about 12 mm.

The difference between the first inner diameter D1 and the second inner diameter D2 ranges from about 0.5 mm to about 46.5 mm. In another embodiment, the difference between the first inner diameter D1 and the second inner diameter D2 ranges from about 0.5 mm to about 20 mm or between about 1 mm and 35 mm.

The first generally frustoconical-shaped portion 36, 136, 236, 436, 536 has a length L1 running along the central longitudinal axis C of the elongated body. The length L1 of the first generally frustoconical-shaped portion 36, 136, 236, 436, 536 ranges from about 100 mm to about 250 mm. The ratio of the length L1 of the first generally frustoconical-shaped portion 36, 136, 236, 436, 536 and the difference between the first inner diameter D1 and the second inner diameter D2 is in a range from about 3 to about 250. In another embodiment, the ratio of the length L1 of the first generally frustoconical-shaped portion 36, 136, 236, 436, 536 and the difference between the first inner diameter D1 and the second inner diameter D2 is in a range from about 30 to about 150.

The difference between the first inner diameter D1 and the second inner diameter D2 can be used in conjunction with the length L1 of the first generally frustoconical-shaped portion 36, 136, 236, 436, 536 to define the angle A1 of the taper first generally frustoconical-shaped portion 36, 136, 236, 436, 536 relative to the central axis of the elongated body.

With reference to FIGS. 1A-1D, 2A-2D, 3A-3D, and 6A-6E, the second generally frustoconical-shaped portion 38, 138, 238, 538 is defined by a third inner diameter D3 proximate one end thereof adjacent the transition from the first generally frustoconical-shaped portion 36, 136, 236, 536 and a fourth inner diameter D4 proximate a second end 42, 142, 242, 242 of the second generally frustoconical-shaped portion 38, 138, 238, 538 adjacent the distal end of the elongated body 12, 112, 212, 512. In embodiments wherein the first generally frustoconical-shaped portion 36, 136, 236, 536 is contiguous with the second generally frustoconical shaped portion 38, 138, 238, 538, the third inner diameter D3 is equal to the second inner diameter D2 and defines the transition T between the first generally frustoconical-shaped portion 36, 136, 236, 536 and the second generally frustoconical-shaped portion 38, 138, 238, 538. In embodiments wherein the first generally frustoconical-shaped portion 36, 136, 236, 536 and the second generally frustoconical-shaped portion are separated by one or more additional sections, the third inner diameter D3 is adjacent the one or more additional sections.

The third inner diameter D3 is greater than the fourth inner diameter D4. The third inner diameter is less than or equal to the second inner diameter D2. The third inner diameter D3 is in a range from about 3.5 mm to about 20 mm. In another embodiment, the third inner diameter D3 is in a range from about 3.5 mm to 12 mm.

The fourth inner diameter D4 is in a range from about 1 mm to about 5 mm. In another embodiment, the fourth inner diameter D4 is in a range from about 2 mm to about 4 mm. In a preferred embodiment, the fourth inner diameter D4 is in a range from about 2 mm to about 3 mm.

The difference between the third inner diameter D3 and the fourth inner diameter D4 ranges from about 0.1 mm to about 17 mm. In another embodiment, the difference between the third inner diameter D3 and the fourth inner diameter D4 ranges from about 0.5 mm to about 10 mm. or between about 1 mm and 15 mm.

The second generally frustoconical-shaped portion 38, 138, 238, 538 has a length running along the central longitudinal axis of the elongated body. The length L2 of the second generally frustoconical-shaped portion 38, 138, 238, 538 is in a range from about 20 mm to about 150 mm. The ratio of the length L2 of the second generally frustoconical-shaped portion 38, 138, 238, 538 and the difference between the third inner diameter D3 and the fourth inner diameter D4 is in a range from about 6 to about 2000. In another embodiment, the ratio of the length L2 of the second generally frustoconical-shaped portion 38, 138, 238, 538 and the difference between the third inner diameter D3 and the fourth inner diameter D4 is in a range from about 10 to about 100.

The difference between the third inner diameter D3 and the fourth inner diameter D4 can be used in conjunction with the length L2 of the second generally frustoconical-shaped portion 38, 138, 238, 538 to define the angle A2 of the taper second generally frustoconical-shaped portion 38, 138, 238, 538 relative to the central axis of the elongated body. In an embodiment, the angle A2 of the taper for the second generally frustoconical-shaped portion 38, 138, 238, 538 is greater than the angle A1 of the first frustoconical-shaped portion 36, 136, 236, 536. In an alternative embodiment, the angle A2 of the taper for the second generally frustoconical-shaped portion 38, 138, 238, 538 is less than the angle A1 of the first generally frustoconical-shaped portion 36, 131, 236, 536.

The ratio of the length L2 of the second generally frustoconical-shaped portion 38, 138, 238, 538 to the length L1 of the first generally frustoconical-shaped portion 36, 136, 236, 536 is in a range from about 0.1 to about 1. In another embodiment, the ratio of the length L2 of the second generally frustoconical-shaped portion 38, 138, 238, 538 to the length L1 of the first generally frustoconical-shaped portion 36, 136, 236, 536 is in a range from about 0.4 to about 1. In another embodiment, the ratio of the length L2 of the second generally frustoconical-shaped portion 38, 138, 238, 538 to the length L1 of the first generally frustoconical-shaped portion 36, 136, 236, 536 is in a range from about 0.5 to about 1. In another embodiment, the ratio of the length L2 of the second generally frustoconical-shaped portion 38, 138, 238, 538 to the length L1 of the first generally frustoconical-shaped portion 36, 136, 236, 536 is in a range from about 0.1 to about 0.2.

With reference to FIGS. 6A-6E, the third generally frustoconical-shaped portion 546 is defined by a fifth inner diameter D5 proximate one end thereof adjacent the transition from the second generally frustoconical-shaped portion 538 and a sixth inner diameter D6 proximate a second end of the third generally frustoconical-shaped portion 546 adjacent the distal end of the elongated body 12, 112, 212, 512. In embodiments wherein the second generally frustoconical-shaped portion 38, 138, 238, 538, is contiguous with the third generally frustoconical shaped portion 546 the fifth inner diameter D5 is equal to the fourth inner diameter D4 and defines the transition T between the second generally frustoconical-shaped portion 38, 138, 238, 538 and the third generally frustoconical-shaped portion 546. In embodiments wherein the second generally frustoconical-shaped portion 38, 138, 238, 538 and the third generally frustoconical-shaped portion 546 are separated by one or more additional sections, the fifth inner diameter D5 is adjacent the one or more additional sections.

The fifth inner diameter D5 is greater than the sixth inner diameter D6. The fifth inner diameter D5 is less than or equal to the fourth inner diameter D4. The fifth inner diameter D5 is in a range from about 3.5 mm to about 18 mm. In another embodiment, the fifth inner diameter D5 is in a range from about 3.5 mm to 10 mm.

The sixth inner diameter D6 is in a range from about 1 mm to about 5 mm. In another embodiment, the sixth inner diameter D6 is in a range from about 2 mm to about 4 mm. In a preferred embodiment, the sixth inner diameter D6 is in a range from about 2 mm to about 3 mm.

The third generally frustoconical-shaped portion 546 has a length running along the central longitudinal axis of the elongated body. The length L3 of the third generally frustoconical-shaped portion 546 is in a range from about 20 mm to about 100 mm.

With reference back to FIGS. 1A-1D, 2A-2D, 3A-3D, 5A-5D, and 6A-6E, the elongated body has a wall thickness defined by the thickness of material between the inner surface 16, 116, 216, 416, 516 and the outer surface 14, 114, 214, 414, 514. In one embodiment, the wall thickness W1, W2 is relatively uniform along the length of the elongated body 12, 112, 212, 412, 512. In this embodiment, the wall thickness is in a range from about 0.5 mm to about 1.3 mm, and preferably in a range from about 0.5 mm to about a 1.0 mm. In an alternative embodiment, the wall thickness is greatest near the proximal end 24, 124, 224, 424, 524 of the intermediate portion and decreases along the length of the elongated body 12, 112, 212, 412, 512 from the proximal end 24, 124, 224, 424, 524 to the distal end 30, 130, 230, 430, 530. In this embodiment, the wall thickness W1 near the proximal end 24, 124, 224, 424, 524 of the elongated body 12, 112, 212, 412, 512 is in a range from about 0.8 mm to about 1.3 mm, and preferably is about 1.0 mm. In this embodiment, the wall thickness W2 near the distal end 30, 130, 230, 430, 530 of the elongated body 12, 112, 212, 412, 512 decreases to a range between about 0.5 mm to about 0.8 mm.

The elongated body 12, 112, 212, 412, 512 has a proximal orifice 20, 120, 220, 420, 520 at the proximal end 24, 124, 224, 242, 524 that is defined by the inner surface 16, 116, 216, 416, 516 of the elongated body 12, 112, 212, 412, 512 at the proximal end 24, 124, 224, 242, 524 of the elongated body 12, 112, 212. In one embodiment, the proximal orifice 20, 120, 220, 420, 520 has an internal diameter in a range from about 4 mm to about 50 mm. In another embodiment the proximal orifice 20, 120, 220, 420, 520 has an internal diameter that is equal to the first inner diameter D1 of the elongated body 12, 112, 212, 412, 512.

The elongated body 12, 112, 212, 412, 512 has a distal orifice 28, 128, 228, 428, 528 at the distal end 30, 130, 230, 430, 530 that is defined by the inner surface 16, 116, 216, 416, 516 of the elongated body 12, 112, 212, 412, 512 at the distal end 30, 130, 230, 430, 530 of the elongated body 12, 112, 212, 412, 512. The internal diameter of the distal orifice 28, 128, 228, 428, 528 is of a size sufficient to allow for a liquid to pass into and out of the lumen 18, 118, 218, 418, 518 of the elongated body 12, 112, 212, 412, 512 in a controlled manner. The distal orifice 28, 128, 228 has an internal diameter in a range from about 1 mm to about 3 mm. In an embodiment, the distal orifice 28, 128, 228, 428, 528 has an internal diameter in a range from about 1.6 mm to about 2.8 mm. In another embodiment, the distal orifice 28, 128, 228, 428, 528 has an internal diameter in a range from about 1.6 mm to about 2.0 mm, or an internal diameter of about 1.8 mm. In another embodiment the distal orifice 28, 128, 228, 428, 528 has an internal diameter that is equal to the fourth inner diameter D4 of the elongated body 12, 112, 212, 412, 512.

The proximal end 24, 124, 224, 242, 524 of the elongated 12, 112, 212, 412, 512 may further include a stem 44, 144, 244, 444, 544 extending therefrom for engaging a differential pressure source, such as a vacuum pump, for controlling the volume of fluid in the lumen 18, 118, 218, 418, 518 of the pipette 10, 110, 210, 410, 510 by allowing a fluid to be drawn into the pipette 10, 110, 210, 410, 510 and subsequently released in a controlled fashion. As seen in FIGS. 1A-1C, 2A-2C, 3A-3D, 5A-5C, and 6A-6C, the stem 44, 144, 244, 444, 544 may be coupled to the proximal end 24, 124, 224, 242, 524 of the pipette 10, 110, 210, 410, 510, such as by routine welding techniques or with an adhesive. In some embodiments such as shown in FIG. 2A-2D, the stem 144 increases the diameter of the proximal end 124 of the elongated body 112. In some embodiments such as shown in FIGS. 1A, 1C, 3A, 3C, 5A, 5C, 6A, and 6C, the stem 44, 244, 444, 544 decreases the diameter of the proximal end 24, 124, 242, 524 of the elongated body 12, 212, 412, 512. The stem 44, 144, 244, 444, 544 may further include a material, such as plug of glass wool, to decrease the likelihood of contamination between the pipette 10, 110, 210, 410, 510 and the differential pressure source.

Figures 4A, 4B:
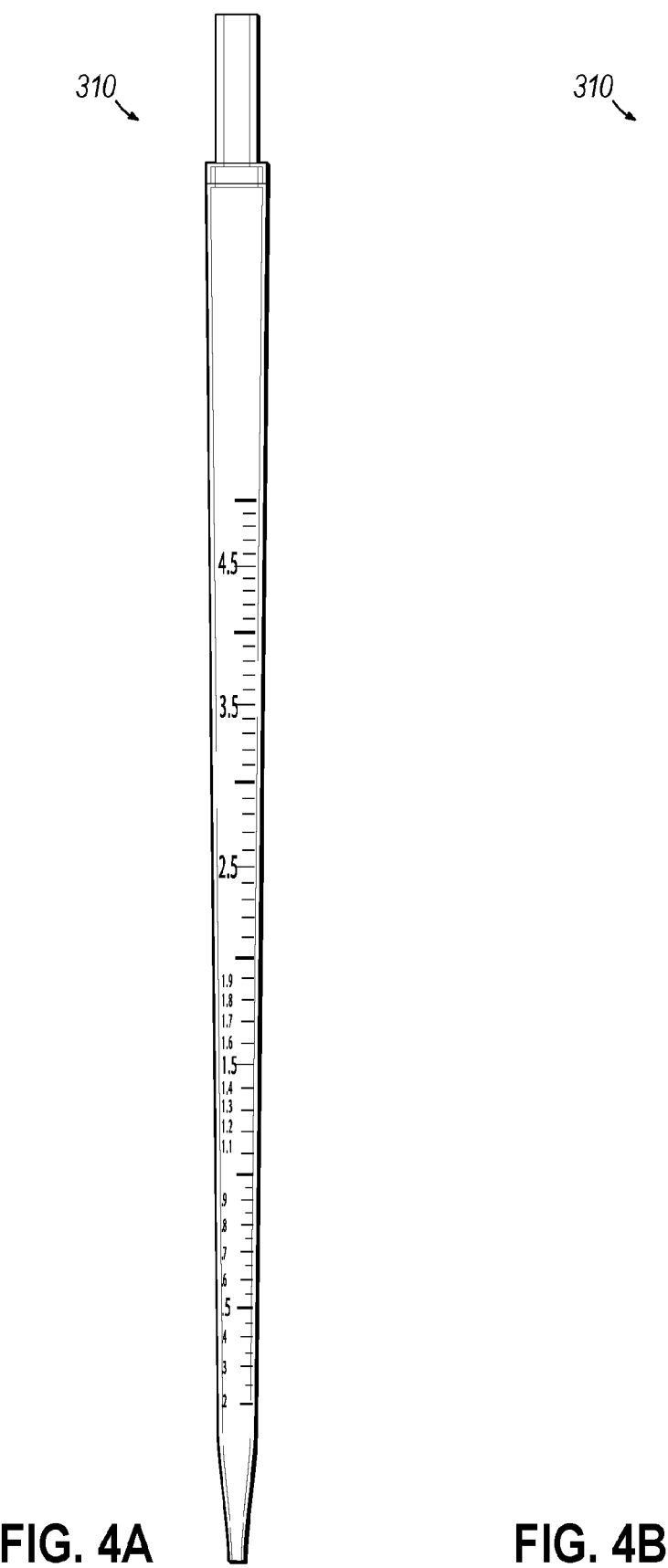
FIG. 4A is an elevated view of a pipette in accordance with embodiments of the invention.
FIG. 4B is an elevated view of a pipette in accordance with embodiments of the invention.
Figure 5A:
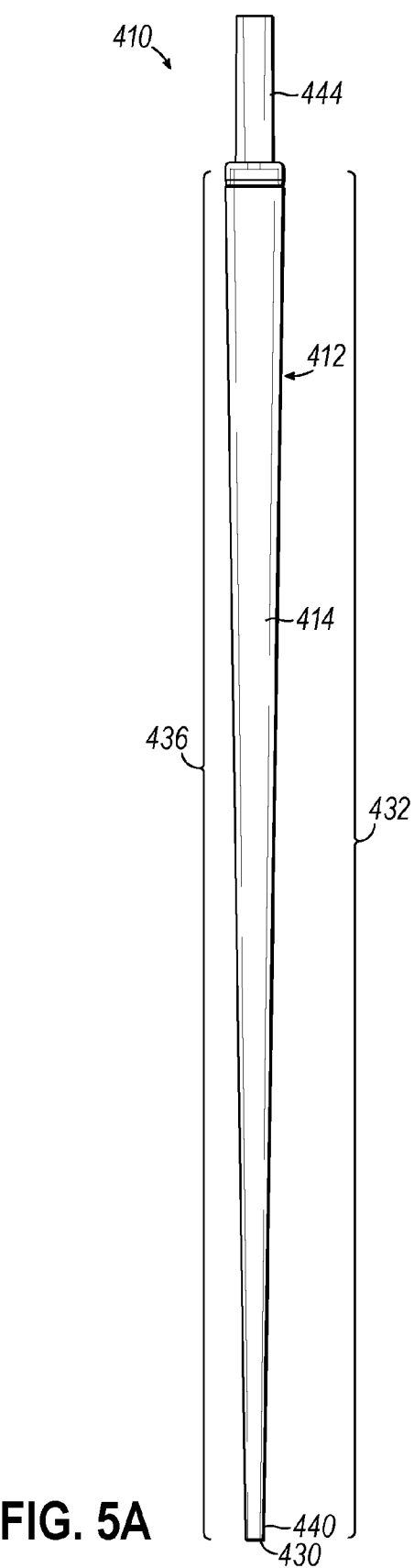
FIG. 5A is an elevated view of a pipette in accordance with embodiments of the invention.
Figure 5B:
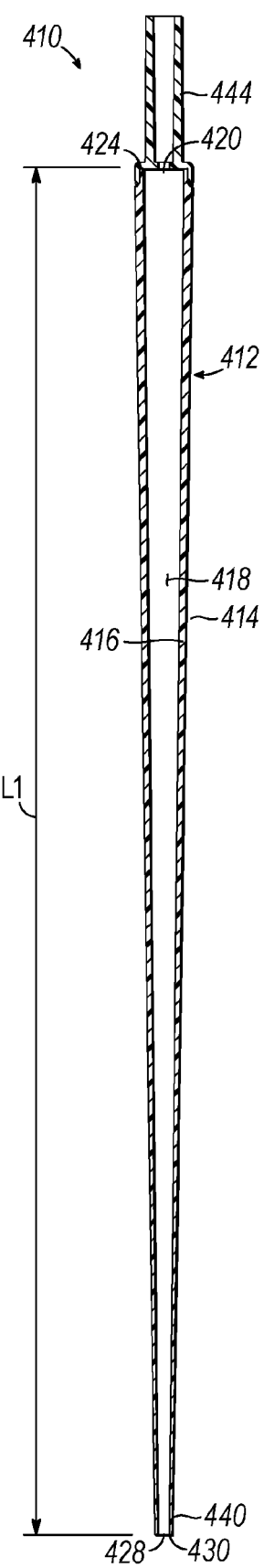
FIG. 5B is a cross section of the pipette of FIG. 5A
Figure 5C:
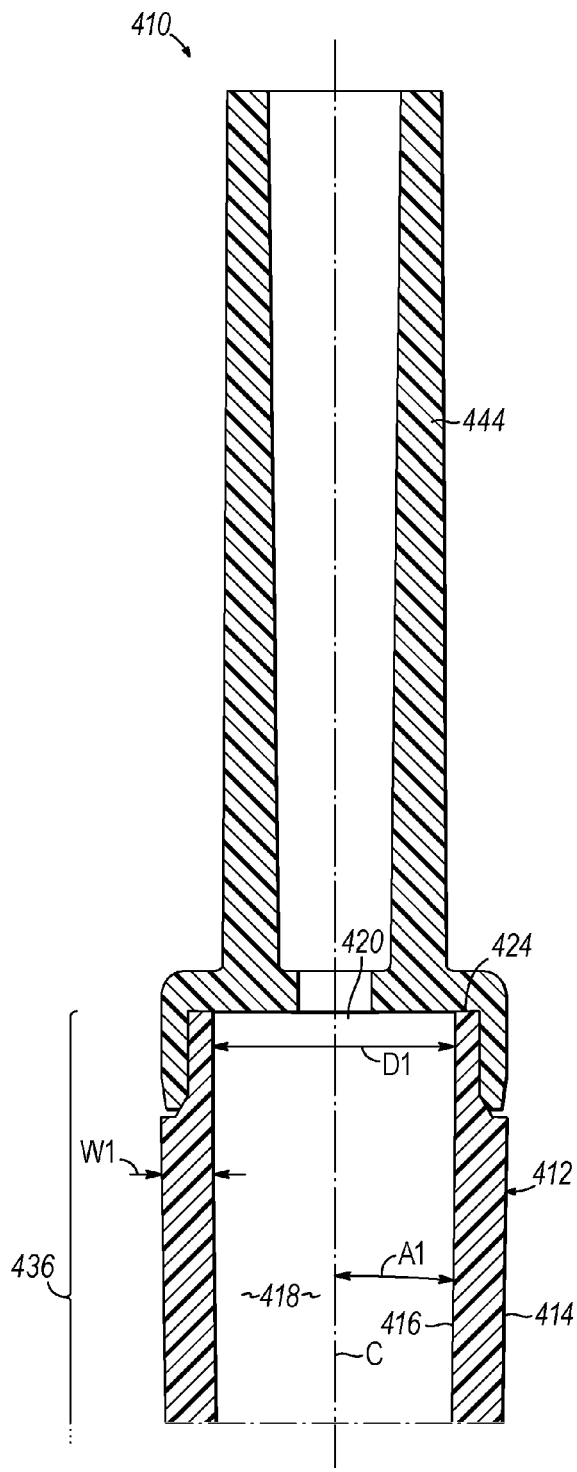
FIG. 5C is a magnified view of an end of the pipette of FIG. 5B.
Figure 5D:
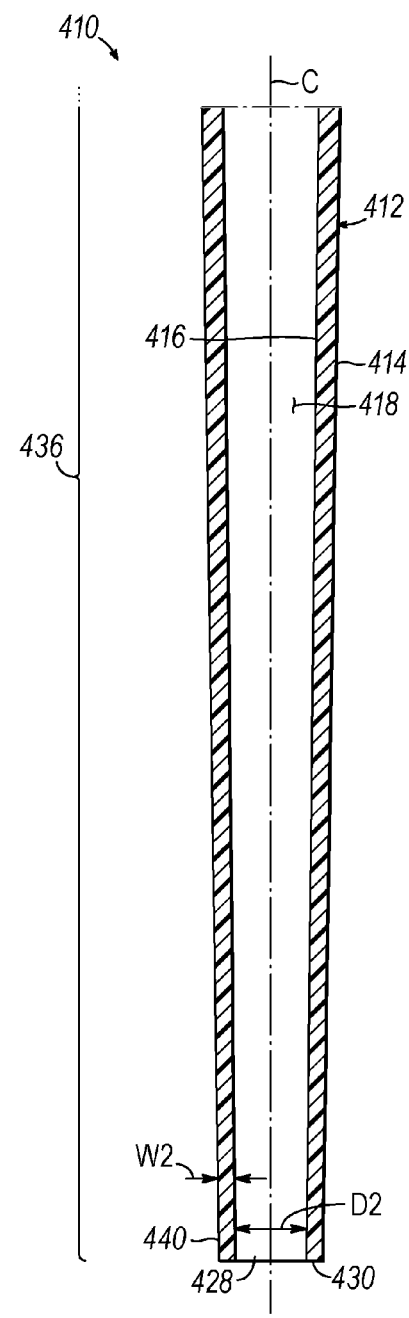
FIG. 5D is a magnified view of an end of the pipette of FIG. 5B.
Figure 6A:
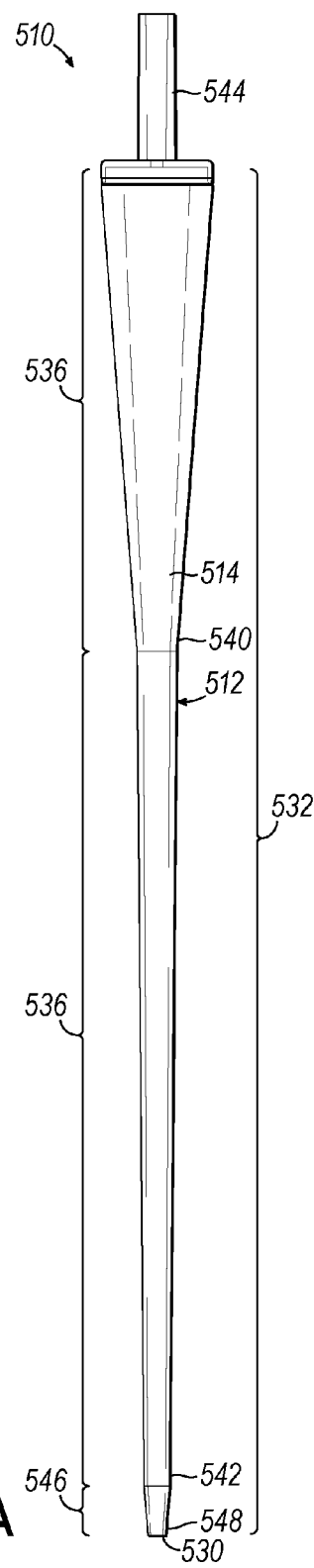
FIG. 6A is an elevated view of a pipette in accordance with embodiments of the invention.
Figure 6B:
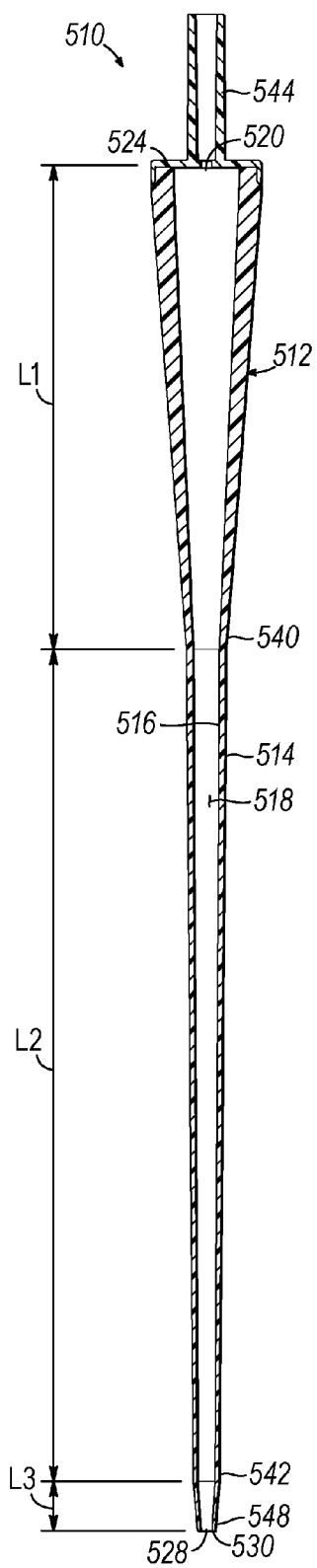
FIG. 6B is a cross section of the pipette of FIG. 6A
Figure 6C:
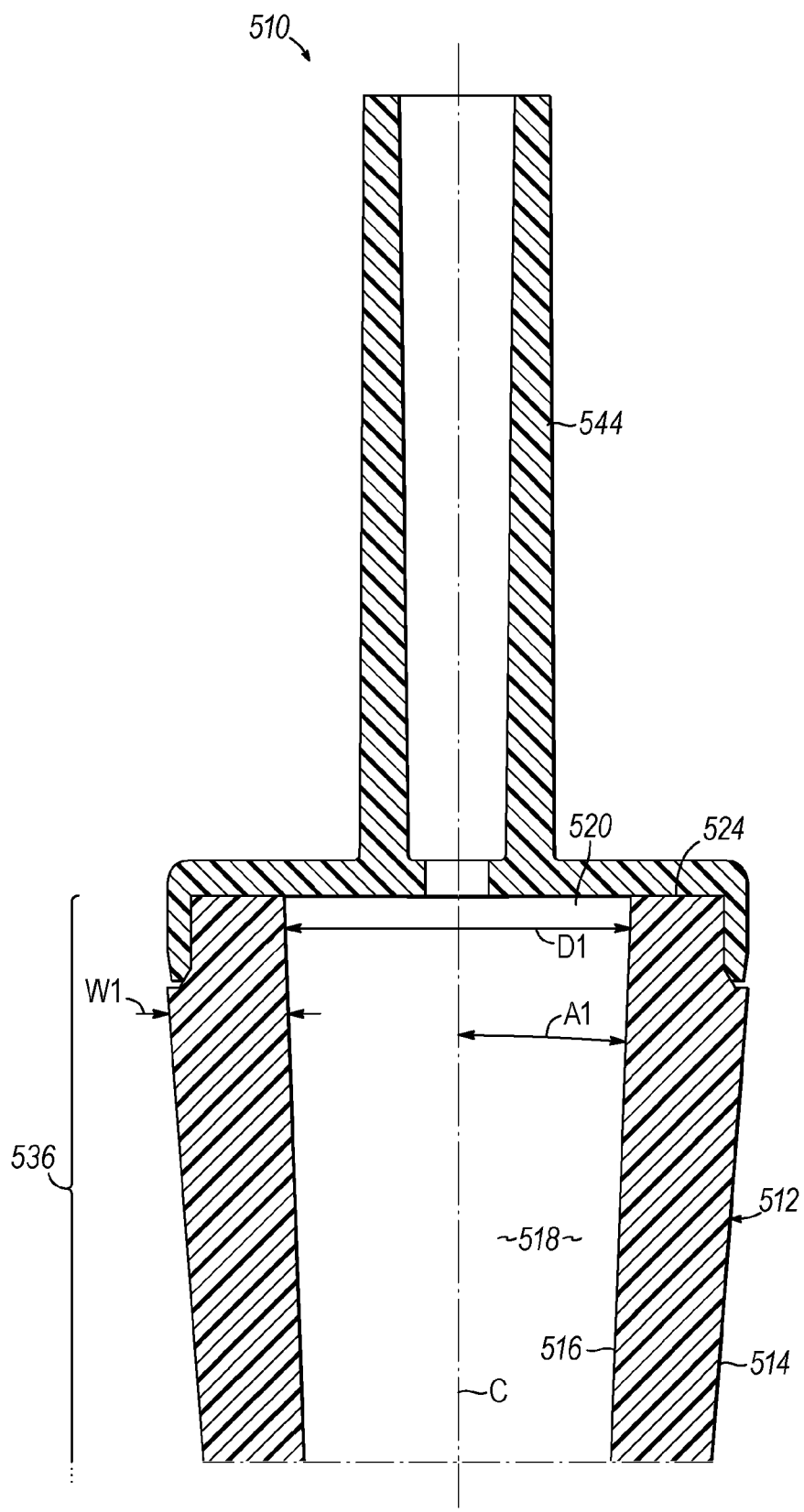
FIG. 6C is a magnified view of an end of the pipette of FIG. 6B.
Figures 6D, 6E:
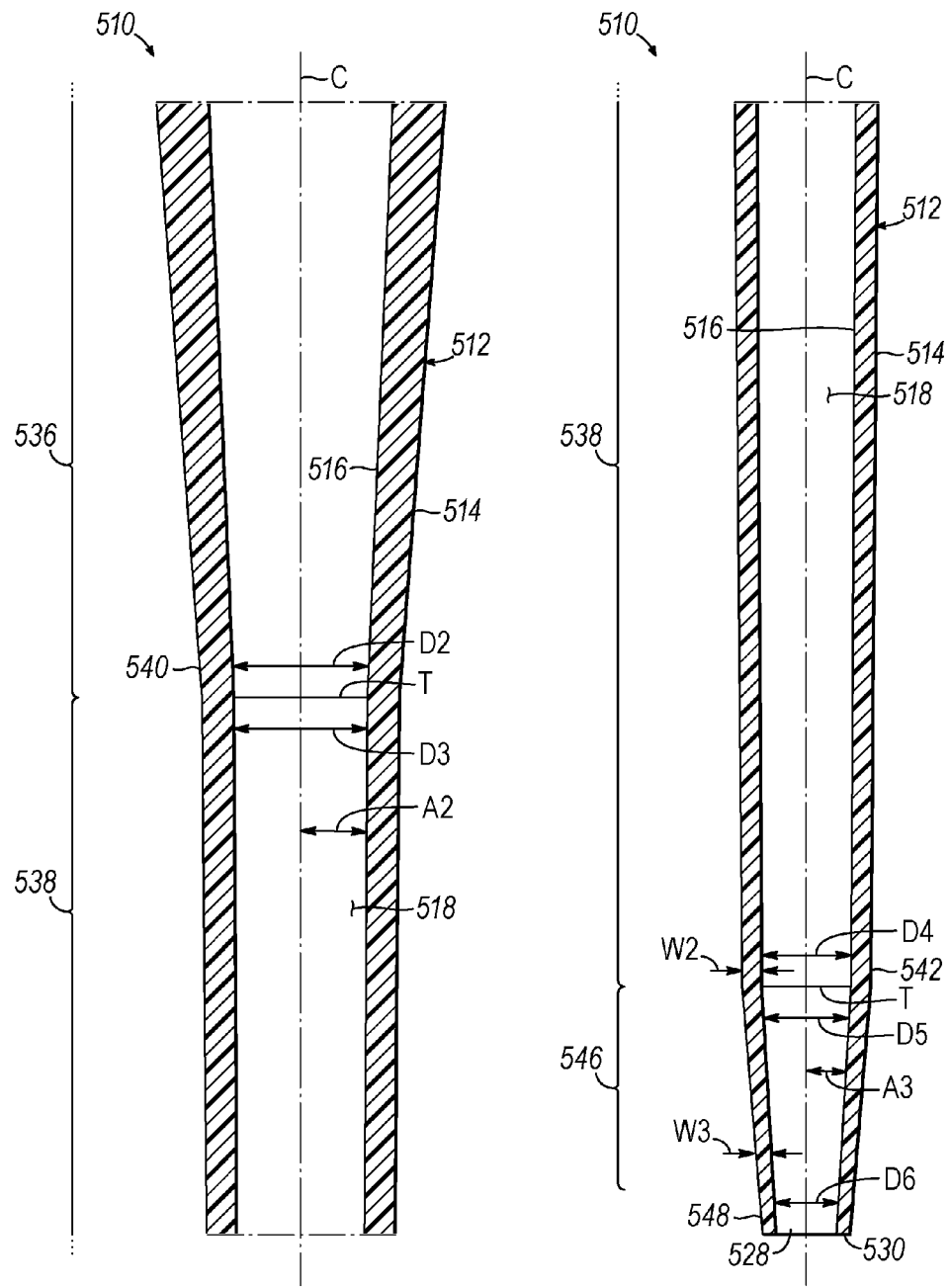
FIG. 6D is a magnified view of an intermediate area of the pipette of FIG. 6B.
FIG. 6E is a magnified view of an end of the pipette of FIG. 6B.

As illustrated in FIGS. 4A and 4B, the pipette 410 includes a plurality of spaced apart graduations. The graduations may be molded on or in a surface of the pipette, be printed on a surface, or be both molded and printed on a surface. Preferably, the surface is the outer surface. The space between adjacent pairs of graduations corresponds to a unit of volume in the lumen. The graduations may include major scale graduations with intermediate and minor scale graduations between the major scale graduations. Arabic numerals may be located proximally to at least some of the graduations. For example, a pipette useful in dispensing a 25 ml total volume may have major scale graduations and Arabic numeral corresponding to each volume of 5 ml, with intermediate graduations corresponding to each volume of 1 ml, and minor scale graduations corresponding to each volume of 0.1 ml. As the inner diameter of the elongated body decreases from the proximal end to the distal end, the volumetric capacity of the lumen per unit of length of elongated body decreases. That is, the volumetric capacity per unit of length of the lumen near distal end is less than the volumetric capacity per unit of length of the lumen near the proximal end. The volumetric capacity of the lumen at any point along the length of the elongated body is determined by taper of the elongated body. Accordingly, the distance between adjacent graduations corresponding to a predetermined volume varies, i.e., decreases, along the length of the elongated body from the distal end toward the proximal end. The variation in the distance between the graduations allows for the increased dispensing accuracy from the pipette as the meniscus of the liquid volume passes the graduation near the distal end of the pipette as compared to the accuracy near the proximal end. In an embodiment, the spacing between adjacent pairs of graduations may indicate different volumes determined by the relative distance of the adjacent pair of graduations from one end of the elongated body. For example, a pair of adjacent graduations near the proximal end may correspond to a greater volume than a pair of adjacent graduations nearer the distal end. In one embodiment, a pair of adjacent graduations near the proximal end corresponds to a volume that is about 2 to about 10 times the volume of a pair of adjacent graduations nearer to the distal end. This results in the pipette having a first region near the proximal end for dispensing larger volumes and a second region nearer the distal end for more accurately dispensing smaller volumes.

Embodiments of the pipette may be formed from a thermoplastic resin suitable for injection molding that is relatively clear when set to allow for viewing the meniscus of the liquid being dispensed therefrom. Exemplary suitable thermoplastic resins include polystyrene, polypropylene, polyethylene, styrene acrylonitrile, cyclic olefin polymer, cyclic olefin copolymer, polycarbonate, polysulfone, polyethylene terephthalate, polymethylmethacrylate, acrylic copolymers, and polymethylpentene.

Standard injection molding process may be used to make pipettes in accordance with embodiments of the invention. Briefly, a mold having a cavity with the desired shape for the outer surface of the pipette is closed around a core having a corresponding first and second generally frustoconical-shaped portions to define a space between core and mold. The core is suspended from knockout bar that includes a stripper which surrounds the upper end of the core.

The thermoplastic resin is introduced into the mold by injectors at a rate predetermined to efficiently fill the mold, generally over a period of time between about 1 and 5 seconds. The resin is injected into the mold near the base of the core. The core is relatively long and thin but has a greater diameter at the base than at the tip. The base of the core corresponds to the proximal end of the elongated body the tip of the core corresponds to the distal end of the pipette. The greater diameter of the base resists the tendency of the core to deflect during the high pressure injection of the thermoplastic resin.

After injection, the resin is allowed to cool for a prescribed period of time before the mold is opened and the knockout bar removes the core from the mold. The stripper then forces the pipette off of the core. As the thermoplastic resin cools, it shrinks onto the core creating a locking force that resists removing the elongated body from the core. An advantage of the dual tapering shape is that when the stripper applies a force to the shrinking resin forming the elongated body of the pipette, the locking force may be overcome simultaneously along the length of the core. This contrasts with injection molded generally cylindrical pipettes in which the locking force between the cylindrical molded body and core must be repeatedly overcome as the stripper forces the molded body from the core. As a result, there is an increased risk of breakage for the relatively long and thin core needed to mold standard generally cylindrical pipettes during removal of the molded body. The dual tapered elongated bodies of pipettes made in accordance with embodiments of the present invention have a decreased risk of breakage due to the simultaneous release of the locking force along the length of the core and molded body. After the pipette is collected, the mold is then closed into the position and the process may be repeated.

EXAMPLE

Exemplary pipettes were designed with measurements as set out in the Table below. For each example, the diameters provided are the outside diameter. The wall thickness for each exemplary pipette varies between about 1.0 mm at the distal end of the elongated body and about 0.5 mm at the proximal end. The overage value is the extra volumetric capacity in addition to the marketed volume expressed as a percentage of the marketed value.

| Example | Marketed Vol. (ml) | distal orifice internal diameter and 4th inner diameter (mm) | second frustoconical-shaped portion length (mm) | Second diameter (mm) | total length (mm) | Proximal orifice internal diameter and 1st inner diameter (mm) | Overage |
|---|---|---|---|---|---|---|---|
| 1 | 1 | 2.8 | 75 | 3.9 | 200 | 6.55 | 10% |
| 2 | 1 | 2.8 | 75 | 3.9 | 200 | 7.64 | 50% |
| 3 | 1 | 2.8 | 75 | 3.9 | 200 | 4.91 | 25% |
| 4 | 1 | 2.8 | 100 | 3.85 | 350 | 5.112 | 25% |
| 5 | 2 | 2.8 | 75 | 5 | 250 | 8 | 10% |
| 6 | 2 | 2.8 | 80 | 6.6 | 250 | 11.5 | 50% |
| 7 | 2 | 2.8 | 75 | 5 | 200 | 8.75 | 25% |
| 8 | 2 | 2.8 | 100 | 4.25 | 350 | 6.75 | 25% |
| 9 | 5 | 2.8 | 90 | 7 | 300 | 8.125 | 10% |
| 10 | 5 | 2.8 | 110 | 7.5 | 300 | 10 | 50% |
| 11 | 5 | 2.8 | 80 | 5 | 200 | 14.5 | 25% |
| 12 | 5 | 2.8 | 100 | 9 | 350 | 8 | 25% |
| 13 | 5 | 1.8 | 20 | 8.7 | 250 | 11 | 50% |
| 14 | 10 | 2.8 | 80 | 9 | 300 | 10.5 | 10% |
| 15 | 10 | 2.8 | 100 | 10 | 300 | 12.75 | 50% |
| 16 | 10 | 2.8 | 85 | 12 | 200 | 14 | 25% |
| 17 | 10 | 2.8 | 100 | 9 | 350 | 10.5 | 25% |
| 18 | 10 | 1.8 | 30 | 10 | 250 | 13 | 40% |
| 19 | 25 | 2.8 | 80 | 6 | 300 | 22 | 10% |
| 20 | 25 | 2.8 | 100 | 10.7 | 300 | 12 | 50% |
| 21 | 25 | 2.8 | 90 | 10 | 200 | 30 | 25% |
| 22 | 25 | 2.8 | 100 | 18 | 350 | 25 | 25% |
| 23 | 50 | 2.8 | 90 | 7.25 | 300 | 31 | 10% |
| 24 | 50 | 2.8 | 100 | 9 | 300 | 36 | 50% |
| 25 | 50 | 2.8 | 100 | 11.75 | 200 | 45 | 25% |

-continued

| Example | Marketed Vol. (ml) | distal orifice internal diameter and 4th inner diameter (mm) | second frustoconical-shaped portion length (mm) | Second diameter (mm) | total length (mm) | Proximal orifice internal diameter and 1st inner diameter (mm) | Overage |
|---|---|---|---|---|---|---|---|
| 26 | 50 | 2.8 | 125 | 7 | 350 | 32 | 25% |
| 27 | 100 | 2.8 | 125 | 12 | 300 | 45 | 10% |
| 28 | 100 | 2.8 | 150 | 20 | 300 | 50 | 50% |
| 29 | 100 | 2.8 | 125 | 20 | 250 | 50 | 25% |
| 30 | 100 | 2.8 | 150 | 17 | 350 | 40 | 25% |

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. For example, the pipettes described herein are described as having a marketed volume, however, one of ordinary skill will appreciate that the maximum capacity of the pipette may exceed the marketed volume in the form of an overage amount. Accordingly, departures may be made from such details without departing from the scope or spirit of the general inventive concept.

What is claimed is:

1. A pipette for dispensing a volume of a liquid, comprising:
    an elongated polymeric body and a stem, the elongated body having an outer surface, an inner surface defining a lumen within the elongated body, a proximal orifice at a proximal end of the elongated body, a distal orifice at a distal end of the elongated body, and a frustoconical-shaped intermediate portion extending therebetween,
    the frustoconical-shaped intermediate portion having a first generally frustoconical-shaped portion, the first generally frustoconical-shaped portion being defined by a first inner diameter proximate one end thereof adjacent the proximal end of the elongated body and a second inner diameter proximate a second end thereof, wherein the first inner diameter is greater than the second inner diameter,
    the distal orifice has an internal diameter in a range from 1 millimeter to 3 millimeters, and
    the stem is permanently coupled to and extends from the proximal end of the elongated body and has an inner diameter that is less than an inner diameter of the proximal orifice of the elongated body.
2. The pipette of claim 1, wherein the internal diameter of the distal orifice is less than the second inner diameter.
3. The pipette of claim 1, wherein the first generally frustoconical-shaped portion has a length in a range from 200 millimeters to 350 millimeters.
4. The pipette of claim 1, wherein the first inner diameter is in a range from 4 millimeters to 50 millimeters.
5. The pipette of claim 1, wherein a difference between the first inner diameter and the second inner diameter is in a range from 0.5 millimeter to 46.5 millimeters.
6. The pipette of claim 1, wherein the proximal orifice has an internal diameter that is equal to the first inner diameter.
7. The pipette of claim 1, wherein a ratio of the length of the first generally frustoconical-shaped portion and a difference between the first inner diameter and the second inner diameter is in a range from 3 to 250.
8. The pipette of claim 1, wherein the frustoconical-shaped intermediate portion has a substantially uniform wall thickness along the length of the elongated body.
9. The pipette of claim 1, wherein the frustoconical-shaped intermediate portion has a wall thickness that decreases along the length of the elongated body from the proximal end to the distal end.
10. The pipette of claim 9, wherein the wall thickness at the proximal end is in a range from 0.5 mm to 1.3 mm.
11. The pipette of claim 1, further comprising a plurality of spaced apart graduations, wherein the distance between pairs of graduations corresponds to a unit of volume in the lumen between the pairs of graduations and the distance between the pairs of graduations varies along the length of the elongated body from the distal end toward the proximal end.
12. The pipette of claim 11, wherein the distance between pairs of graduations corresponding to a unit of volume decreases along the length of the elongated body from the distal end toward the proximal end.
13. The pipette of claim 11, wherein the elongated body includes a first pair of graduations that corresponds to a first unit of volume and a second pair of graduations that corresponds to a second unit of volume that is less than the first unit of volume, wherein the second pair of graduations is nearer to the distal end of the elongated body relative to the first pair of graduations.
14. The pipette of claim 13, wherein the first unit of volume is in a range from between 2 to 10 times greater than the second unit of volume.
15. The pipette of claim 1, further comprising a plurality of spaced apart graduations wherein the distance between pairs of graduations corresponds to a unit of volume in the lumen between the pairs of graduations and the distance between the pairs of graduations varies along the length of the elongated body from the distal end toward the proximal end.
16. The pipette of claim 15, wherein the internal diameter of the distal orifice is equal to the fourth inner diameter.
17. The pipette of claim 15, wherein the second generally frustoconical-shaped portion has a length in a range from 20 millimeters to 150 millimeters.
18. The pipette of claim 15, wherein at least one of the second inner diameter and the third inner diameter are in a range from 3.5 millimeters to 20 millimeters.
19. The pipette of claim 15, wherein at least one of the second inner diameter and the third inner diameter is in a range from 3.5 millimeters to 12 millimeters.

20. The pipette of claim 15, wherein the second inner diameter is equal to the third inner diameter.

21. The pipette of claim 15, wherein the first generally frustoconical-shaped portion is contiguous with the second generally frustoconical-shaped portion.

22. The pipette of claim 15, wherein a difference between the third inner diameter and the fourth inner diameter is in a range from 0.1 millimeters to 17 millimeters.

23. The pipette of claim 15, wherein a ratio of the length of the second generally frustoconical-shaped portion to the first generally frustoconical-shaped portion is in a range from 0.1 to 1.

24. The pipette of claim 15, wherein a ratio of the length of the second generally frustoconical-shaped portion and the difference between the third inner diameter and the fourth inner diameter is in a range from 6 to 2000.

25. The pipette of claim 15, further comprising a plurality of spaced apart graduations wherein the distance between pairs of graduations corresponds to a unit of volume in the lumen between the pairs of graduations and the distance between the pairs of graduations varies along the length of the elongated body from the distal end toward the proximal end.

26. The pipette of claim 25, wherein the first generally frustoconical-shaped portion includes a first pair of graduations that corresponds to a first unit of volume and the second generally frustoconical-shaped portion includes a second pair of graduations that corresponds to a second unit of volume, and the first unit of volume is greater than the second unit of volume.

27. The pipette of claim 26, wherein the first unit of volume is in a range from between 2 to 10 times greater than the second unit of volume.

28. The pipette of claim 27, wherein the distance between the second pair of graduations is greater than the distance between the first pair of graduations.

29. The pipette of claim 1, wherein the stem is welded or affixed with an adhesive to the proximal end of the elongated body.

* * * * *

UNITED STATES PATENT AND TRADEMARK OFFICE
CERTIFICATE OF CORRECTION

PATENT NO. : 10,343,156 B2
APPLICATION NO. : 13/835663
DATED : July 9, 2019
INVENTOR(S) : John M. Staton et al.

It is certified that error appears in the above-identified patent and that said Letters Patent is hereby corrected as shown below:

In the Specification

In Column 2, Lines 32-33, change "Long thin core pins use to generate highly accurate pipettes" to --Long thin core pins used to generate highly accurate pipettes--.

In Column 4, Lines 35-36, change "similar to the pipettes illustrated FIGS. 1A, 2A, and 3A" to --similar to the pipettes illustrated in FIGS. 1A, 2A, and 3A--.

In Column 4, Lines 40-41, change "The pipette has an outer surface 414 and in inner surface" to --The pipette has an outer surface 414 and an inner surface--.

In Column 4, Line 47, change "In yet another embodiment illustrated in FIG. 6A-6E," to --In yet another embodiment illustrated in FIGS. 6A-6E,--.

In Column 4, Lines 51-52, change "The pipette has an outer surface 514 and in inner surface" to --The pipette has an outer surface 514 and an inner surface--.

In Column 5, Lines 42-44, change "of the first generally frustoconical-shaped portion 36, 136, 236, 436, 536 to define the angle A1 of the taper first generally frustoconical-shaped portion" to --of the first generally frustoconical-shaped portion 36, 136, 236, 436, 536 to define the angle A1 of the taper of the first generally frustoconical-shaped portion--.

In Column 6, Lines 33-36, change "can be used in conjunction with the length L2 of the second generally frustoconical-shaped portion 38, 138, 238, 538 to define the angle A2 of the taper second generally frustoconical-shaped portion" to --can be used in conjunction with the length L2 of the second generally frustoconical-shaped portion 38, 138, 238, 538 to define the angle A2 of the taper of the second generally frustoconical-shaped portion--.

In Column 7, Line 39, change "and preferably in a range from about 0.5 mm to about a 1.0 mm." to --and preferably in a range from about 0.5 mm to about 1.0 mm.--.

Signed and Sealed this
Twelfth Day of November, 2019

Andrei Iancu
*Director of the United States Patent and Trademark Office*

CERTIFICATE OF CORRECTION (continued)
U.S. Pat. No. 10,343,156 B2

In Column 8, Lines 17-18, change "The proximal end 24, 124, 224, 242, 524 of the elongated 12, 112, 212, 412, 512 may further include" to --The proximal end 24, 124, 224, 242, 524 of the elongated body 12, 112, 212, 412, 512 may further include--.

In Column 8, Line 29, change "some embodiments such as shown in FIG. 2A-2D," to --some embodiments such as shown in FIGS. 2A-2D,--.

In Column 8, Lines 35-36, change "may further include a material, such as plug of glass wool," to --may further include a material, such as a plug of glass wool,--.

In Column 10, Lines 1-2, change "corresponds to the proximal end of the elongated body the tip of the core corresponds" to --corresponds to the proximal end of the elongated body and the tip of the core corresponds--.

In the Claims

In Claim 15, Column 12, Lines 50-56, change "15. The pipette of claim 1, further comprising a plurality of spaced apart graduations wherein the distance between pairs of graduations corresponds to a unit of volume in the lumen between the pairs of graduations and the distance between the pairs of graduations varies along the length of the elongated body from the distal end toward the proximal end." to --15. The pipette of claim 1, wherein the frustoconical-shaped intermediate portion further comprises: a second generally frustoconical-shaped portion being defined by a third inner diameter proximate one end thereof adjacent a transition to the first generally frustoconical-shaped portion and a fourth inner diameter proximate a second end thereof adjacent the distal end of the elongated body, wherein the third inner diameter is greater than the fourth inner diameter.--.

In Claim 18, Column 12, Lines 63-64, change "the third inner diameter are in a range from 3.5 millimeters to 20 millimeters." to --the third inner diameter is in a range from 3.5 millimeters to 20 millimeters.--.

In Claim 22, Column 13, Line 8, change "a range from 0.1 millimeters to 17 millimeters." to --a range from 0.1 millimeter to 17 millimeters.--.